(12) United States Patent
Horiuchi et al.

(10) Patent No.: US 6,404,844 B1
(45) Date of Patent: Jun. 11, 2002

(54) TOMOGRAPHIC IMAGING SCAN CONDITION DETERMINING METHOD, TOMOGRAPHIC IMAGING METHOD AND X-RAY CT APPARATUS

(75) Inventors: Tetsuya Horiuchi; Makoto Gohno, both of Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/718,165

(22) Filed: Nov. 21, 2000

(30) Foreign Application Priority Data

Dec. 13, 1999 (JP) ............................. 11-352638

(51) Int. Cl.$^7$ ................................................ A61B 6/03
(52) U.S. Cl. ............................................. 378/8; 378/16
(58) Field of Search ................................. 378/15, 16, 8, 378/48, 45

(56) References Cited

U.S. PATENT DOCUMENTS

| | | | |
|---|---|---|---|
| 5,379,333 A | * 1/1995 | Toth | 378/16 |
| 5,485,494 A | 1/1996 | Williams | 378/16 |
| 6,141,398 A | 10/2000 | He et al. | 378/4 |
| 6,141,402 A | * 10/2000 | Toth | 378/150 |

FOREIGN PATENT DOCUMENTS

| | | |
|---|---|---|
| EP | 0981998 | 3/2000 |
| EP | 0982001 | 3/2000 |
| JP | 09075334 | 3/1997 |
| JP | 9238935 | 9/1997 |
| JP | 09313472 | 12/1997 |
| JP | 11104121 | 4/1999 |

\* cited by examiner

*Primary Examiner*—David P. Porta
*Assistant Examiner*—Therese Barber
(74) *Attorney, Agent, or Firm*—Moonray Kojima (57) ABSTRACT

For the purpose of determining a radiation dose without excess or insufficiency with respect to an allowed value of image noise in performing a helical scan by a CT apparatus comprising a multi-detector, a method comprises the steps of: selecting an image thickness of an X-ray tomographic image to be produced by a helical scan by an X-ray CT apparatus comprising a multi-detector (Step ST1); provisionally determining an X-ray dose in obtaining the X-ray tomographic image having the image thickness by single-slice CT using a single-slice CT radiation dose determining algorithm (Step ST2); selecting a scan protocol (Step ST3); reading a dose correction factor from a dose correction factor table that matches the selected image thickness (Step ST4); correcting the X-ray dose by the dose correction factor (Step ST5); determining tomographic imaging scan conditions by specifying at least one of the tube current and the emission time (Step ST6); and performing the helical scan and displaying an X-ray tomographic image (Step ST7). Consequently, a disadvantage that a subject is exposed more than necessary can be prevented.

14 Claims, 3 Drawing Sheets

FIG. 4 Dose Correction Factor Table 8 (Image thickness; 5 mm)

| No. | Imaging table movement speed [mm/rotation] | X-ray beam width at scan center [mm] | Dose correction factor |
|---|---|---|---|
| 1 | 7.5 | 2.5 | 0.68 |
| 2 | 11.25 | 3.75 | 0.69 |
| 3 | 15.0 | 5.0 | 0.85 |
| 4 | 15.0 | 2.5 | 1.34 |
| 5 | 22.5 | 3.75 | 1.38 |
| 6 | 30.0 | 5.0 | 1.32 |

FIG. 5

START X-ray Tomographic Imaging Process

ST 1: Select image thickness

ST 2: Provisionally determine X-ray dose value scan_mAs for obtaining X-ray tomographic image by performing axial scan to have same slice thickness as image slice thickness with desired image noise value, based on single-slice CT X-ray dose determining algorithm ST 3: Select scan protocol ST 4: Read dose correction factor from dose correction factor table ST 5: Correct X-ray dose scan_mAs by dose correction factor ST 6: Specify tube current or emission time according to corrected X-ray dose scan_mAs; Determine tomographic imaging scan conditions ST 7: Perform helical scan; Produce X-ray tomographic image; Display image

END

TOMOGRAPHIC IMAGING SCAN CONDITION DETERMINING METHOD, TOMOGRAPHIC IMAGING METHOD AND X-RAY CT APPARATUS

BACKGROUND OF THE INVENTION

The present invention relates to a tomographic imaging scan condition determining method, tomographic imaging method and X-ray CT (computed tomography) apparatus, and more particularly to a tomographic imaging scan condition determining method, tomographic imaging method and X-ray CT apparatus that can determine a radiation dose without excess or insufficiency with respect to an allowed value of image noise.

Figure 1:
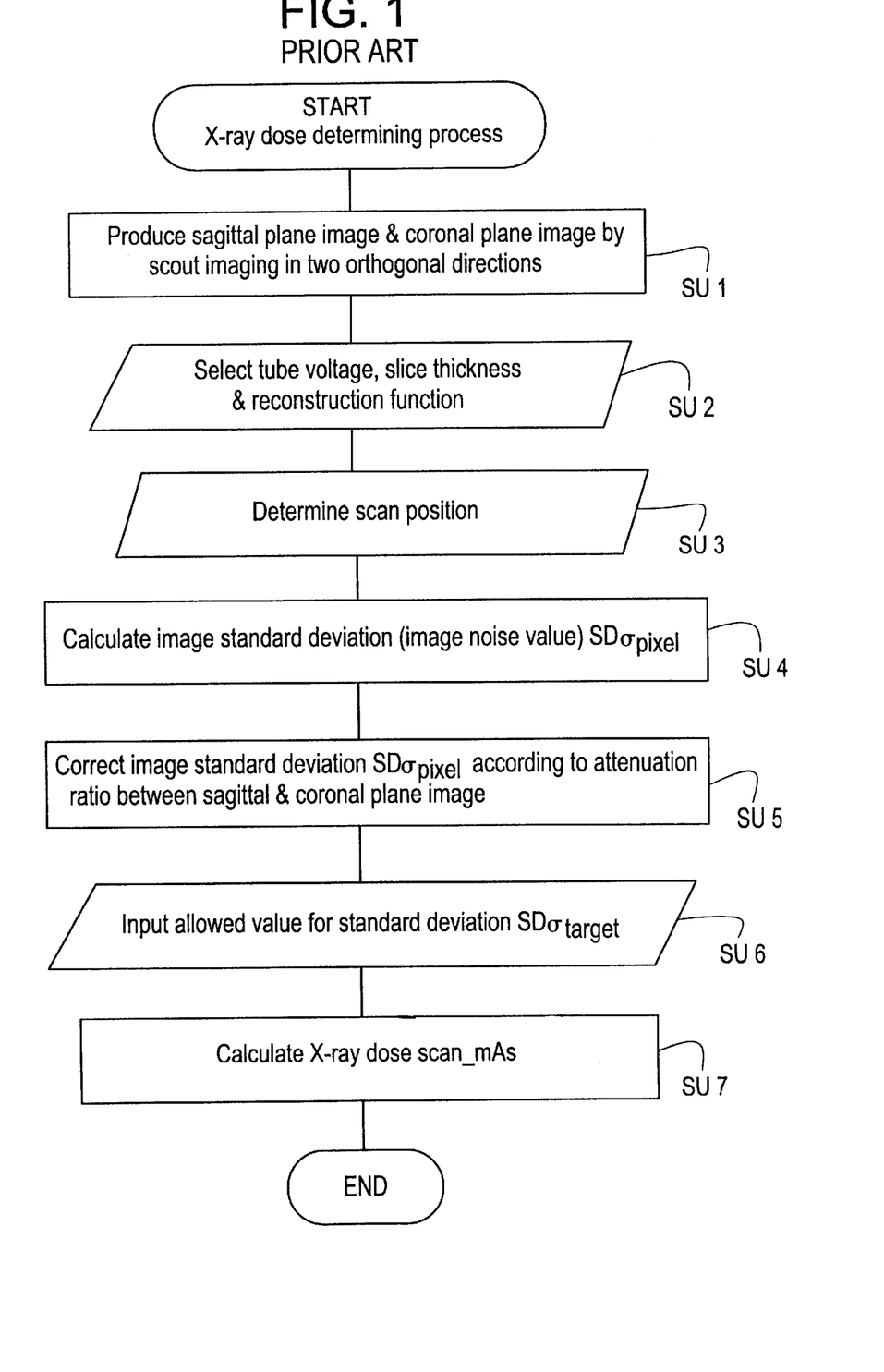
FIG. 1 is a flow chart of an example of a conventional X-ray dose determining process.

FIG. 1 is a flow chart showing an example of a conventional X-ray dose determining process in an X-ray CT apparatus comprising a single detector, i.e., a detector having one detector row.

In Step SU1, scout imaging is performed in two orthogonal directions to produce a sagittal plane image and a coronal plane image.

In Step SU2, a tube voltage, slice thickness and reconstruction function are selected.

In Step SU3, a scan position (slice position) in X-ray tomographic imaging is determined with reference to the scout images.

In Step SU4, a standard deviation $SD\sigma_{pixel}$ of an image SD assuming the cross section of the subject to be circular is calculated based on a projected area $S_{object}$ in imaging a subject at default imaging conditions, a default X-ray dose default_mAs (which is the product of the tube current and the emission time) and a slice thickness Th, as follows:

$$SD\sigma_{pixel} \approx \sqrt{\frac{S_{object}}{(\text{default\_mAs} \times Th)}}.$$

The standard deviation $SD\sigma_{pixel}$ is regarded as an image noise value.

The projected area $S_{object}$ is roughly evaluated from the sagittal and coronal plane images.

In Step SU5, the standard deviation $SD\sigma_{pixel}$ is corrected according to the attenuation ratio between the sagittal plane image and coronal plane image to obtain a standard deviation $SD\sigma'_{pixel}$ according to the actual cross-sectional shape of the subject.

In Step SU6, an allowed value $SD\sigma_{target}$ for the standard deviation (image noise value) of the image SD is input.

In Step SU7, an X-ray dose scan_mAs satisfying the standard deviation $SD\sigma_{target}$ is calculated for each slice as follows:

$$\text{scan\_mAs} = \text{default\_mAs} \times \left(\frac{SD\sigma'_{pixel}}{SD\sigma_{target}}\right)^2.$$

The basic principle of an X-ray dose determining process like the above is disclosed in, for example, Japanese Patent Application Laid Open No. H11-104121.

Recently, a technique has been developed involving performing a helical scan by an X-ray CT apparatus comprising a multi-detector, i.e., a detector having a plurality of detector rows arranged in parallel, and combining weighted data of respective slices (multislice) corresponding to the rows of the multi-detectors for image reconstruction, to thereby increase the substantial slice thickness, or image thickness. That is, even when the X-ray beam width is decreased, an X-ray tomographic image with a large image thickness can be obtained by using an extended range of data in image reconstruction (i.e., by increasing the number of rotations of the X-ray tube and multi-detector to more than one). In this case, the X-ray dose required to obtain an X-ray tomographic image with the same image noise value can be reduced compared to that by one rotation.

However, since the X-ray CT apparatus comprising the multi-detector still employs the X-ray dose determining process for the conventional single-slice CT (see FIG. 1), the actual image noise level is greater or smaller than the allowed image noise value at some scan conditions. When the actual image noise level is greater than the allowed value, required image quality cannot be achieved; and when the actual image noise level is smaller, the X-ray dose is unnecessarily large.

SUMMARY OF THE INVENTION

It is an object of the invention to provide a tomographic imaging scan condition determining method, tomographic imaging method and X-ray CT apparatus that can determine a radiation dose without excess or insufficiency with respect to an allowed value of image noise in performing a helical scan by a CT apparatus comprising a multi-detector.

In accordance with a first aspect of the invention, there is provided a tomographic imaging scan condition determining method comprising the steps of: when a tomographic image having an image thickness is to be produced by a helical scan by a CT apparatus comprising a multi-detector having a plurality of detector rows arranged in parallel, provisionally determining a radiation dose in obtaining the tomographic image by single-slice CT using a single-slice CT radiation dose determining algorithm; correcting the radiation dose such that an image noise value of the tomographic image obtained by performing the helical scan is not excessive or insufficient with respect to an allowed value; and determining tomographic imaging scan conditions proper for the corrected radiation dose.

In the tomographic imaging scan condition determining method of the first aspect, a radiation dose provisionally determined to obtain a tomographic image having a certain image thickness is corrected so that an image noise value of the tomographic image obtained by performing a helical scan is not excessive or insufficient with respect to an allowed value. Therefore, a minimum radiation dose satisfying an image noise value requirement can be accurately calculated.

Thus, a disadvantage that required image quality cannot be achieved due to an insufficient radiation dose can be avoided, and a subject can be prevented from unnecessary exposure due to an excessive radiation dose. Moreover, since the most suitable radiation dose can be determined automatically or semi-automatically, the complexity is reduced for a human operator.

In accordance with a second aspect of the invention, there is provided a tomographic imaging scan condition determining method comprising the steps of: selecting an image thickness of a tomographic image to be produced by a helical scan by a CT apparatus comprising a multi-detector having a plurality of detector rows arranged in parallel; provisionally determining a radiation dose in obtaining the tomographic image having said image thickness by a single-slice CT using a single-slice CT radiation dose determining algorithm; selecting scan conditions of the helical scan to be performed; correcting said provisionally determined radiation dose to a radiation dose such that an image noise value of the tomographic image obtained by performing the helical scan at said scan conditions is not excessive or insufficient with respect to an allowed value; and determining tomographic imaging scan conditions proper for said corrected radiation dose.

The tomographic imaging scan condition determining method of the second aspect achieves the same effects as in the tomographic imaging scan condition determining method of the first aspect. Moreover, the image thickness of an X-ray tomographic image to be produced can be selected. Furthermore, scan conditions for a helical scan can be selected.

In accordance with a third aspect of the invention, there is provided a tomographic imaging scan condition determining method as described regarding the first or second aspect, comprising the step of preferentially specifying either an electric current to be supplied to an emitting source or an emission time, in order to emit radiation with the corrected radiation dose.

In the tomographic imaging scan condition determining method of the third aspect, when the electric current to be supplied to an emitting source is preferentially specified, the emitting source can be assuredly prevented from being overloaded. When the emission time is preferentially specified, the scan time can be adjusted in consideration of an effect of subject's body motion on the image quality etc.

In accordance with a forth aspect of the invention, there is provided a tomographic imaging scan condition determining method as described the second or third aspect, comprising the step of adjusting the image thickness by altering at least one of a weighting function in combining data of the rows of said multi-detector for image reconstruction, a radiation beam width, and a movement speed of an imaging table for placing a subject.

In the tomographic imaging scan condition determining method of the fourth aspect, when a weighting function for image reconstruction is altered, the image thickness can be adjusted by a calculational process only, without mechanical control. When the radiation beam width is altered, the image thickness can be adjusted by, for example, controlling the opening width of a collimator aperture. When the movement speed of an imaging table is altered, the image thickness can be adjusted by controlling a drive system of the imaging table.

In accordance with a fifth aspect of the invention, there is provided a tomographic imaging scan condition determining method as described regarding any one of the first through fourth aspects, comprising the step of correcting the radiation dose with a dose correction factor based on a reference value, the reference value being a radiation dose in performing an axial scan with a slice thickness equal to the image thickness.

In the tomographic imaging scan condition determining method of the fifth aspect, the radiation dose is corrected with a dose correction factor based on a radiation dose in an axial scan. Therefore, a radiation dose proper for scan conditions can be calculated by a simple calculation.

In accordance with a sixth aspect of the invention, there is provided a tomographic imaging method, comprising the step of producing a tomographic image by performing a helical scan at the tomographic imaging scan conditions determined by the tomographic imaging scan condition determining method as described regarding any one of the first through fifth aspects.

In the tomographic imaging method of the sixth aspect, a tomographic image is produced using tomographic imaging scan conditions determined by the aforementioned tomographic imaging scan condition determining method. Therefore, a tomographic image with required image quality can be obtained by a minimum exposure.

In accordance with a seventh aspect of the invention, there is provided a tomographic imaging scan condition determining method comprising the steps of: when an X-ray tomographic image having an image thickness is to be produced by a helical scan by an X-ray CT apparatus comprising a multi-detector having a plurality of detector rows arranged in parallel, provisionally determining an X-ray dose in obtaining said X-ray tomographic image by single-slice CT using a single-slice CT X-ray dose determining algorithm; selecting scan conditions for the helical scan to be performed; correcting said X-ray dose to an X-ray dose such that an image noise value of the X-ray tomographic image obtained by performing the helical scan at said scan conditions is not excessive or insufficient with respect to an allowed value; and determining tomographic imaging scan conditions proper for said corrected X-ray dose.

In the tomographic imaging scan condition determining method of the seventh aspect, a disadvantage that image quality of an X-ray tomographic image is extremely degraded due to an insufficient X-ray dose can be avoided, and a subject can be prevented from unnecessary exposure due to an excessive X-ray dose.

In accordance with an eighth aspect of the invention, there is provided the tomographic imaging scan condition determining method as described regarding the seventh aspect, comprising the step of preferentially specifying either an X-ray tube current or an emission time in order to emit X-rays with the corrected X-ray dose.

In the tomographic imaging scan condition determining method of the eighth aspect, when the X-ray tube current is preferentially specified, the X-ray tube is assuredly prevented from being overloaded and decreased in lifetime. When the emission time is preferentially specified, the scan time can be adjusted in consideration of an effect of subject's body motion on the image quality etc.

In accordance with a ninth aspect of the invention, there is provided a tomographic imaging scan condition determining method as described regarding the seventh or eighth aspect, comprising the step of correcting said X-ray dose with a dose correction factor based on a reference value, said reference value being an X-ray dose in performing an axial scan with a slice thickness equal to said image thickness.

In the tomographic imaging scan condition determining method of the ninth aspect, the X-ray dose is corrected based on an X-ray dose in an axial scan. Therefore, an X-ray dose proper for scan conditions can be calculated by a simple calculation.

In accordance with a tenth aspect of the invention, there is provided a tomographic imaging scan condition determining method as described regarding the ninth aspect, comprising the steps of: obtaining a dose correction factor that expresses an X-ray dose by a multiplying factor based on a reference value, said reference value being an X-ray dose in performing an axial scan by single-slice CT on a phantom imitating a CT value distribution of a standard subject with a slice thickness equal to a desired image thickness, said X-ray dose being an X-ray dose for obtaining an X-ray tomographic image by a helical scan employing a multi-detector with an image noise value equivalent to that in said axial scan; and correcting said X-ray dose by multiplying said provisionally determined X-ray dose by said dose correction factor.

In the tomographic imaging scan condition determining method of the tenth aspect, the X-ray dose is corrected with a dose correction factor based on an X-ray dose in performing an axial scan on a phantom. Therefore, an X-ray dose proper for imaging of a subject can be calculated with good accuracy.

In accordance with a eleventh aspect of the invention, there is provided a tomographic imaging method, comprising the step of producing an X-ray tomographic image by performing a helical scan at the tomographic imaging scan conditions determined by the tomographic imaging scan condition determining method as described regarding any one of the seventh through tenth aspects.

In the tomographic imaging method of the eleventh aspect, an X-ray tomographic image is produced using tomographic imaging scan conditions determined by the aforementioned tomographic imaging scan condition determining method. Therefore, an X-ray tomographic image with required image quality can be obtained by a minimum exposure.

In accordance with a twelfth aspect of the invention, there is provided an X-ray CT apparatus comprising: an X-ray tube for emitting X-rays; a multi-detector having a plurality of detector rows arranged in parallel; X-ray dose provisionally determining means for, when an X-ray tomographic image having an image thickness is to be produced by a helical scan employing said multi-detector, provisionally determining an X-ray dose in obtaining said X-ray tomographic image by single-slice CT using a single-slice CT X-ray dose determining algorithm; X-ray dose correcting means for correcting said provisionally determined X-ray dose to an X-ray dose such that an image noise value of the X-ray tomographic image obtained by performing the helical scan is not excessive or insufficient with respect to an allowed value; and scan control means for performing control of the helical scan conforming to said corrected X-ray dose.

In the X-ray CT apparatus of the twelfth aspect, an X-ray dose provisionally determined to obtain an X-ray tomographic image having a certain image thickness is corrected so that an image noise value of the X-ray tomographic image is not excessive or insufficient with respect to an allowed value. Therefore, a minimum X-ray dose satisfying an image noise value requirement can be accurately calculated, and a helical scan conforming to the condition can be performed.

Thus, a disadvantage that required image quality cannot be achieved due to an insufficient X-ray dose can be avoided, and a subject can be prevented from unnecessary X-ray exposure due to an excessive X-ray dose.

In accordance with a thirteenth aspect of the invention, there is provided an X-ray CT apparatus comprising: an X-ray tube for emitting X-rays; a multi-detector having a plurality of detector rows arranged in parallel; image thickness selecting means for selecting an image thickness of an X-ray tomographic image to be produced by a helical scan employing said multi-detector; X-ray dose provisionally determining means for provisionally determining an X-ray dose in obtaining the X-ray tomographic image having said image thickness by single-slice CT using a single-slice CT X-ray dose determining algorithm; scan condition selecting means for selecting scan conditions for the helical scan to be performed; X-ray dose correcting means for correcting said provisionally determined X-ray dose to an X-ray dose such that an image noise value of the X-ray tomographic image obtained by performing the helical scan at said scan conditions is not excessive or insufficient with respect to an allowed value; and scan control means for performing control of the helical scan conforming to said corrected X-ray dose.

The X-ray CT apparatus of the thirteenth aspect achieves the same effects as in the X-ray CT apparatus of the twelfth aspect. Moreover, the image thickness of an X-ray tomographic image to be produced can be selected using image thickness selecting means. Furthermore, scan conditions for a helical scan can be selected using scan condition selecting means.

In accordance with a fourteenth aspect of the invention, there is provided an X-ray CT apparatus comprising: an X-ray tube for emitting X-rays; a multi-detector having a plurality of detector rows arranged in parallel; image thickness selecting means for selecting an image thickness of an X-ray tomographic image to be produced by a helical scan employing said multi-detector; X-ray dose provisionally determining means for provisionally determining an X-ray dose in obtaining the X-ray tomographic image having said image thickness by single-slice CT using a single-slice CT X-ray dose determining algorithm; scan condition selecting means for selecting scan conditions for the helical scan to be performed; a dose correction factor table for storing a dose correction factor for each image thickness and each scan condition; dose correcting means for correcting said provisionally determined X-ray dose by reading a dose correction factor corresponding to said selected image thickness and scan conditions out of said correction factor table and multiplying said provisionally determined X-ray dose by said dose correction factor; and scan control means for performing control of the helical scan conforming to said corrected X-ray dose.

The X-ray CT apparatus of the fourteenth aspect achieves the same effects as in the X-ray CT apparatus of the thirteenth aspect. Moreover, the X-ray dose is corrected by using a dose correction factor read out of a dose correction factor table corresponding to a slice thickness and scan conditions to be achieved. Therefore, a radiation dose proper for scan conditions can be calculated by a simple calculation.

In accordance with a fifteenth aspect of the invention, there is provided an X-ray CT apparatus as described regarding the fourteenth aspect, wherein said dose correction factor table is created corresponding to a plurality of image thicknesses which may be selected, and stores a dose correction factor that expresses an X-ray dose by a multiplying factor based on a reference value, said reference value being an X-ray dose in performing an axial scan by single-slice CT on a phantom imitating a CT value distribution of a standard subject with a slice thickness equal to a desired image thickness, said X-ray dose being an X-ray dose for obtaining an X-ray tomographic image by a helical scan employing said multi-detector with an image noise value equivalent to that in said axial scan.

In the X-ray CT apparatus of the fifteenth aspect, the X-ray dose is corrected with a dose correction factor based on an X-ray dose in performing an axial scan on a phantom. Therefore, an X-ray dose proper for imaging of a subject can be calculated with good accuracy.

In accordance with a sixteenth aspect of the invention, there is provided an X-ray CT apparatus as described regarding the fourteenth or fifteemth aspect, wherein said dose correction factor table stores a dose correction factor for each moving speed of an imaging table and X-ray beam width at a scan center.

In the X-ray CT apparatus of the sixteenth aspect, a dose correction factor is stored in a dose correction factor table for each movement speed of an imaging table and X-ray beam width frequently used as scan conditions. Therefore, the clinical ease-of-use and imaging efficiency can be further improved.

According to the tomographic imaging scan condition determining method and tomographic imaging method of the present invention, the radiation dose to a subject is reduced to a minimum that satisfies an image noise value requirement. Therefore, a disadvantage that the subject is exposed more than necessary can be prevented.

Moreover, according to the X-ray CT apparatus of the present invention, an X-ray tomographic image that satisfies an image noise value requirement can be obtained with a minimum X-ray dose. Therefore, safety can be further improved.

Further objects and advantages of the present invention will be apparent from the following description of the preferred embodiments of the invention as illustrated in the accompanying drawings.

DETAILED DESCRIPTION OF THE INVENTION

The present invention will now be described in more detail with reference to embodiments shown in the accompanying drawings. It should be noted that the present invention is not limited thereto.

Figure 2:
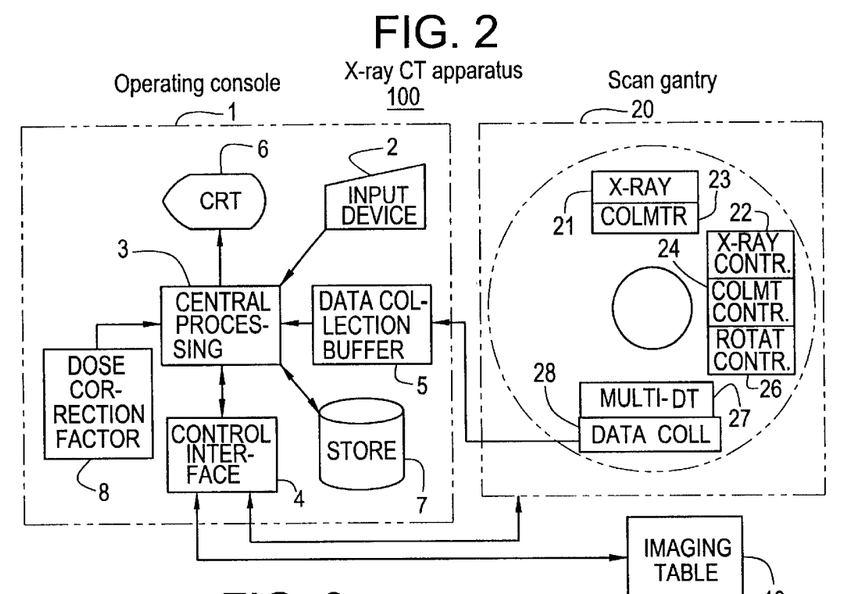
FIG. 2 is a block diagram illustrating an X-ray CT apparatus in accordance with an embodiment of the present invention.

FIG. 2 is a block diagram of an X-ray CT apparatus in accordance with an embodiment of the present invention.

The X-ray CT apparatus 100 comprises an operating console 1, an imaging table 10 and a scan gantry 20.

The operating console 1 comprises an input device 2 for receiving a command or information input supplied by a human operator, a central processing apparatus 3 for executing an X-ray tomographic imaging process including a process for provisionally determining an X-ray dose required for a helical scan, a control interface 4 for exchanging a control signal and the like with the imaging table 10 and the scan gantry 20, a data collection buffer 5 for collecting data acquired at the scan gantry 20, a CRT 6 for displaying an X-ray tomographic image reconstructed from the data, a storage device 7 for storing a program, data and an X-ray tomographic image, and a dose correction factor table 8 for storing dose correction factors to correct the provisionally determined X-ray dose.

The scan gantry 20 comprises an X-ray tube 21, an X-ray controller 22, a collimator 23, a collimator controller 24, a rotation controller 26 for rotating the X-ray tube 21 and the like around a scan center (designated as SC in FIG. 3), a multi-detector 27 having four rows of detectors arranged in parallel, and a data collecting section 28 for collecting data extracted from the multi-detector 27.

Figure 3:
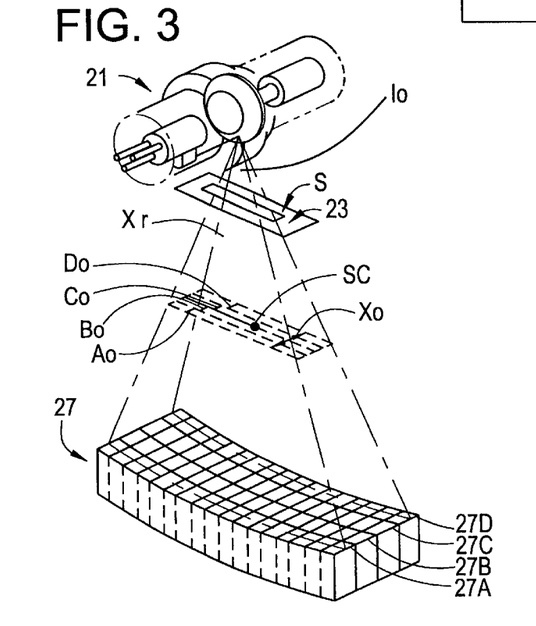
FIG. 3 is a schematic view illustrating an X-ray tube, collimator and multi-detector.

FIG. 3 is a schematic view illustrating the X-ray tube 21, collimator 23 and multi-detector 27.

An X-ray Io emitted from the X-ray tube 21 is formed into a flat X-ray beam Xr after passing through an aperture S of the collimator 23, and impinges upon first through fourth detector rows 27A–27D of the multi-detector 27.

The opening width and position of the aperture S of the collimator 23 is regulated by the collimator controller 24 based on an instruction from the central processing apparatus 3.

The width of the X-ray beam Xr at the scan center SC is referred to as X-ray beam width Xo. The width of a portion of the X-ray beam width Xo that impinges upon the first detector row 27A is first slice thickness Ao; the width of a portion that impinges upon the second detector row 27B is second slice thickness Bo; the width of a portion that impinges upon the third detector row 27C is third slice thickness Co; and the width of a portion that impinges upon the fourth detector row 27D is fourth slice thickness Do.

Figure 4:
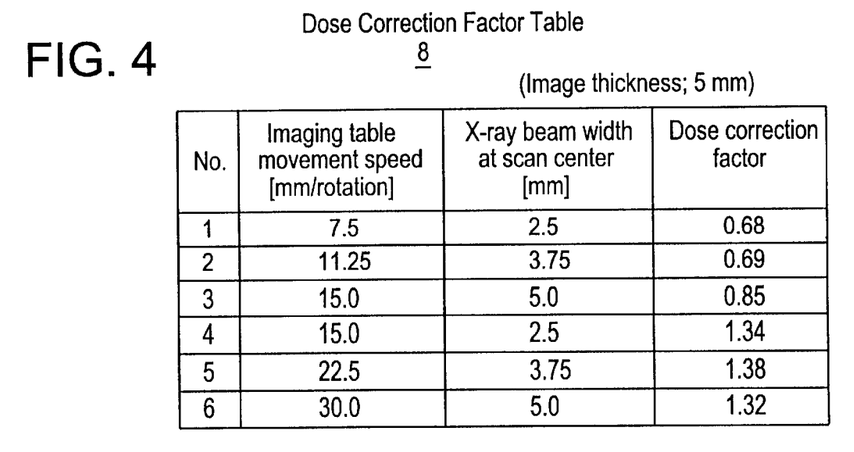
FIG. 4 is an explanatory diagram illustrating the content of a dose correction factor table.

FIG. 4 is an explanatory diagram illustrating the content of the dose correction factor table 8. The illustrated table corresponds to an image thickness IT=5 mm. The factors for other image thicknesses IT that may be selected are stored in the same format.

In the table 8, a dose correction factor is stored beforehand for each movement speed [mm/rotation] of the imaging table 10 and X-ray beam width Xo [mm] at the scan center SC. The dose correction factor expresses an X-ray dose by a multiplying factor based on a reference value, wherein the reference value is an X-ray dose in performing an axial scan by single-slice CT on a phantom imitating a CT value distribution of a standard subject with a slice thickness Th=IT, and the X-ray dose is an X-ray dose for obtaining an X-ray tomographic image by a helical scan with an image thickness IT employing the multi-detector 27 to have an image noise value equivalent to that in the axial scan.

Generally, as the movement speed of the imaging table 10 becomes smaller (i.e., as "No." in FIG. 4 becomes smaller), the image quality of the X-ray tomographic image improves. On the other hand, as the moving speed of the imaging table 10 becomes larger (i.e., as "No." in FIG. 4 becomes larger), the emission time decreases.

Figure 5:
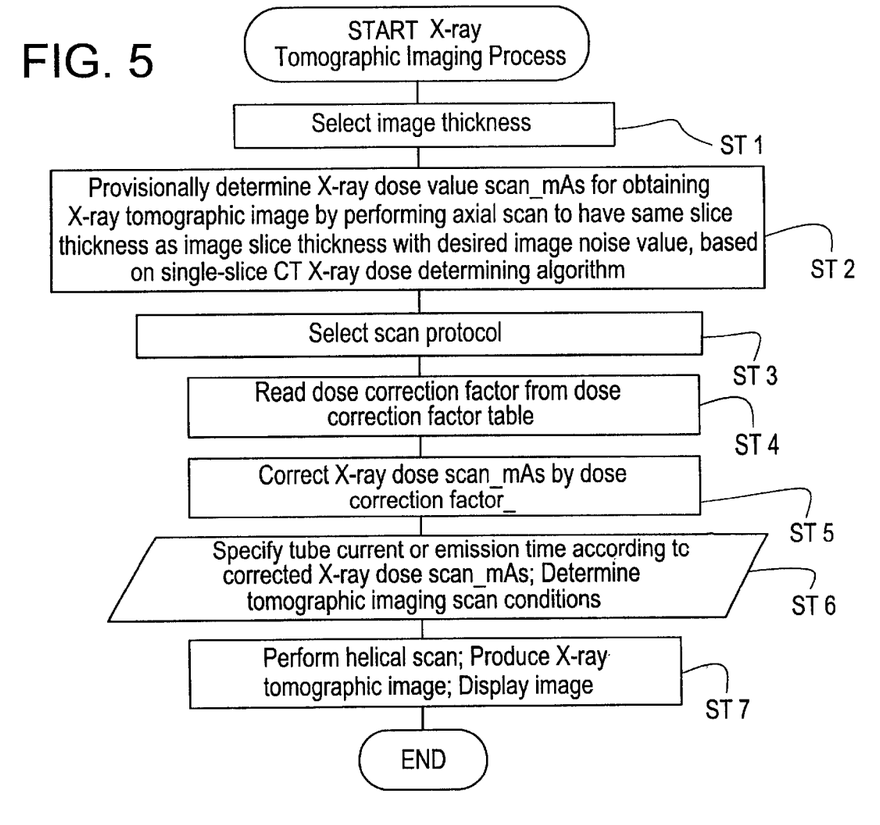
FIG. 5 is a flow chart of an X-ray tomographic imaging process by the X-ray CT apparatus of FIG. 2.

FIG. 5 is a flow chart illustrating an X-ray tomographic imaging process by the X-ray CT apparatus 100 of FIG. 2.

In Step ST1, the operator selects an image thickness IT For example, an image thickness IT of 5 mm is selected. Adjustment of the image thickness IT is performed by, for example, altering one of the weighting for combining data extracted from the first through fourth detector rows 27A–27D, the X-ray beam width Xo at the scan center SC, and the movement speed of the imaging table 10. A technique for adjusting the image thickness by altering a weighting function for use in interpolating data collected by an X-ray CT apparatus comprising a multi-detector is disclosed in, for example, Japanese Patent Application Laid Open No. H9-238935.

In Step ST2, an X-ray dose scan_mAs for obtaining an X-ray tomographic image by performing an axial scan to have the same slice thickness as the image slice thickness IT with a desired image noise value is provisionally determined based on a single-slice CT X-ray dose determining algorithm, such as the X-ray dose determining process described earlier with reference to FIG. 1. For example, the X-ray dose is provisionally determined as scan_mAs=200 [mAs].

In Step ST3, the operator selects a scan protocol for a helical scan to be performed. For example, a movement speed of the imaging table 10 of 7.5 [mm/rotation] and an X-ray beam width Xo of 2.5 [mm] are selected.

In Step ST4, a dose correction factor corresponding to the table movement speed and the X-ray beam width Xo is read out of a dose correction factor table 8 that matches the selected image thickness IT. In the above example, a dose correction factor of 0.68 is read out corresponding to No. 1 in the dose correction factor table 8 of FIG. 4.

In Step ST5, the X-ray dose scan_mAs determined at Step ST2 is multiplied by the read-out dose correction factor to correct the X-ray dose. In the above example, a corrected X-ray dose scan_mAs of 136 [mAs] is obtained from X-ray dose 200 [mAs]×0.68.

In Step ST6, the operator specifies at least one of the tube current and emission time according to the corrected X-ray dose scan_mAs to determine tomographic imaging scan conditions. (The scan conditions may be determined automatically without intervention by the operator.) For example, if the tube current is specified as 100 [mAs], the emission time is determined as 1.36 [s]. If the emission time is specified as 0.8 [s], the tube current is determined as 170 [mAs]. When the tube current is preferentially specified, the X-ray tube 21 is assuredly prevented from being overloaded and decreased in life time. When the emission time is preferentially specified, the scan time can be adjusted in consideration of an effect of body motion on the image quality etc.

In Step ST7, a helical scan is performed for imaging a predefined site based on the determined tomographic imaging scan conditions to produce an X-ray tomographic image with an image thickness IT for display.

According to the above-described X-ray CT apparatus 100, a radiation dose provisionally determined by a single-slice CT X-ray dose determining algorithm is corrected so that the image noise value of an X-ray tomographic image obtained by a helical scan is not excessive or insufficient with respect to an allowed value. Therefore, X-ray exposure to a subject can be reduced to a minimum.

Many widely different embodiments of the invention may be configured without departing from the spirit and the scope of the present invention. It should be understood that the present invention is not limited to the specific embodiments described in the specification, except as defined in the appended claims.

What is claimed is:

1. A tomographic imaging scan condition determining method utilizing a CT apparatus comprising a multi-detector having a plurality of detector rows arranged in parallel and helically scanned to produce a tomographic image having an image thickness, wherein said method comprises the steps of:

priorly storing in table form a dose correction factor according to at least a radiation beam width used in said CT apparatus and imaging carrier movement speed for different image thicknesses for obtaining tomographic images which have imaging noise within a range of acceptable imaging noise;

determining a provisional radiation dose for obtaining said tomographic image by a single slice CT using a single slice radiation dose determining algorithm;

obtaining from said table form stored dose correction factor corresponding to a selected movement speed and beam width for a particular image thickness;

correcting said provisional radiation dose by multiplying with said obtained dose correction factor to provide a corrected radiation dose; and determining tomographic imaging scan conditions for obtaining said corrected radiation dose so as to obtain tomographic images with image noise within said acceptable range.

2. A tomographic imaging scan condition determining method utilizing a CT apparatus comprising a multi-detector having a plurality of detector rows arranged in parallel which is helically scanned to produce a selected image thickness of a tomographic image, wherein said method comprises the steps of:

priorly storing in table form a dose correction factor according to at least a radiation beam width used in said CT apparatus and imaging carrier movement speed for different image thicknesses for obtaining tomographic images which have imaging noise within a range of acceptable imaging noise;

determining a provisional radiation dose for obtaining said tomographic image having said image thickness by a single slice CT using a single slice radiation dose determining algorithm;

selecting scan conditions of helical scanning to be performed;

accessing the stored table form to obtain dose correction factor corresponding to a selected imaging carrier movement speed and radiation beam width for a particular image thickness;

correcting said provisional radiation dose by multiplying with the accessed does correction factor to obtain a corrected radiation dose; and determining tomographic image scanning conditions from the selected scan conditions for obtaining said corrected radiation dose so as to obtain tomographic images with imaging noise within said acceptable range.

3. The method of claim 1 or 2, further comprising the step of specifying either an electric current to be supplied to an emitting source of radiation in said CT apparatus or an emission time, in order to emit radiation with said corrected radiation dose.

4. The method of claim 1 or 2, further comprising the step of:

adjusting said image thickness by altering at least one of a weighting factor in combining data of said rows of said multi-detector for image reconstruction, a radiation beam width and movement speed of said imaging carrier.

5. The method of claim 1 or 2, wherein said dose correction factor is based on a reference value, said reference value being a radiation dose in performing an axial scan with a slice thickness equal to said image thickness.

6. A tomographic image scanning condition determining method utilizing an X-ray CT apparatus comprising a multi-detector having a plurality of detector rows arranged in parallel which is helically scanned to produce an X-ray tomographic image having an image thickness, wherein said method comprises the steps of:

priorly storing in table form a dose correction factor according to at least an X-ray beam width used in said X-ray CT apparatus and imaging carrier movement speed for different image thicknesses for obtaining tomographic images which have imaging noise within an acceptable range of imaging noise;

determining a provisional X-ray dose for obtaining said tomographic image having said image thickness by a single slice CT using a single slice X-ray dose determining algorithm;

selecting scan conditions of helical scanning to be performed;

accessing the stored table form to obtain dose correction factor corresponding to a selected imaging carrier movement speed and X-ray beam width for a particular image thickness;

correcting said provisional X-ray dose by multiplying with the accessed dose correction factor to obtain a corrected X-ray dose; and determining tomographic image scanning conditions from the selected scan conditions for obtaining said corrected X-ray dose so as to obtain tomographic images with imaging noise within said acceptable range.

7. The method of claim 6, further comprising the step of preferentially specifying either an X-ray tube current or an emission time in order to emit X-rays wit said corrected X-ray dose.

8. The method of claim 6, wherein said dose correction factor is based on a reference value, said reference value being an X-ray dose in performing an axial scan with a slice thickness equal to said image thicknesses.

9. The method of claim 1, 2 or 8, wherein said dose correction factor expresses an X-ray dose by a multiplying factor based on a reference value, said reference value being an X-ray dose in performing an axial scan by single slice CT on a phantom initiating a CT value distribution of a standard subject with a slice thickness equal to a desired image thickness, said X-ray dose being an X-ray dose for obtaining an X-ray tomographic image by a helical scan using said multi-detector with an image noise value equivalent to that in said axial scan, and correcting said X-ray dose by multiplying said provisional X-ray dose by said dose correction factor.

10. The method of claim 1, 2, or 3, further comprising the step of performing a helical scan at the obtained scanning conditions thereby to produce a tomographic image.

11. A CT apparatus comprising:

means for emitting radiation;

a multi-detector having a plurality of detector rows arranged in parallel;

means for helically scanning said multi-detector to produce a tomographic image having an image thickness;

means for priorly storing in table form a dose correction factor according to at least a radiation beam width of a radiation emitted by said means for emitting radiation and movement speed of an imaging table for different image thicknesses for obtaining tomographic images which have imaging noise within a range of acceptable imaging noise;

said imaging table;

means for determining a provisional radiation dose for obtaining said tomographic image by a single slice CT using a single slice radiation dose determining algorithm;

means for obtaining from said table form stored dose correction factor corresponding to a selected movement speed of said imaging table and beam width of said radiation for a particular image thickness;

means for correcting said provisional radiation dose by multiplying with said obtained dose correction factor to provide a corrected radiation dose; and means for determining tomographic imaging scan conditions for obtaining said corrected radiation dose so as to obtain tomographic images with image noise within said accepted range.

12. A CT apparatus comprising:

means for emitting radiation;

an imaging table;

a multi-detector having a plurality of detector rows arranged in parallel;

means for helically scanning said multi-detector to produce a tomographic image;

a means for selecting an image thickness from said tomographic image;

means for priorly storing in table form a dose correction factor according to at least a radiation beam width of a radiation emitted by said means for emitting radiation and movement speed of said imaging table for different image thicknesses for obtaining tomographic images which have imaging noise within a range of acceptable imaging noise;

means for determining a provisional radiation dose for obtaining said tomographic image having said selected image thickness by a single slice CT using a single slice radiation dose determining algorthim;

means for selecting scan conditions of helical scanning to be performed;

means for accessing said stored table form to obtain dose correction factor corresponding to a selected movement speed of said imaging table and a radiation beam width for said selected image thickness;

means for correcting said provisional radiation dose by multiplying with the accessed dose correction factor to obtain a corrected radiation dose; and means for determining tomographic image scanning conditions from the selected scan conditions for obtaining said corrected radiation dose so as to obtain tomographic images with imaging noise within said acceptable range.

13. An X-ray CT apparatus comprising:

means for emitting X-ray radiation;

an imaging table;

a multi-detector having a plurality of detector rows arranged in parallel;

means for helically scanning said multi-detector to produce a tomographic image having an image thickness;

means for priorly storing in table form a dose correction factor according to an X-ray beam width of said x-ray radiation from said means for emitting X-ray radiation and movement speed of said imaging table for different image thicknesses for obtaining tomographic images which have imaging noise within an acceptable range of imaging noise;

means for determining a provisional X-ray dose for obtaining said tomographic image having said image thickness by a single slice CT using a single slice X-ray dose determining algorthim;

means for selecting scan conditions of helical scanning to be performed;

means for accessing the stored table form to obtain dose correction factor corresponding to a selected movement speed of said imaging table and X-ray beam width for a particular image thickness;

means for correcting said provisional X-ray dose by multiplying with the accessed dose correction factor to obtain a corrected X-ray dose; and means for determining tomographic image scanning conditions from the selected scan conditions for obtaining said corrected X-ray dose so as to obtain tomographic images with imaging noise within said acceptable range.

14. The apparatus of claim 12, 13 or 14, wherein said stored table form is created corresponding to a plurality of image thicknesses which may be selected, and stores a dose correction factor that expresses a radiation dose by a multiplying factor based on a reference value, said reference value being a radiation dose used in performing axial scan by single slice CT on a phantom initiating a CT value distribution of a standard subject with a slice thickness equal to a desired image thickness, said radiation dose being an X-ray dose for obtaining an X-ray tomographic image by a helical scan employing said multi-detector with an image noise value equivalent to that in said axial scan.

* * * * *